(12) United States Patent
Abe

(10) Patent No.: US 7,282,025 B2
(45) Date of Patent: Oct. 16, 2007

(54) ELECTRONIC ENDOSCOPE APPARATUS FOR CONNECTION TO ADAPTER UNIT

(75) Inventor: Kazunori Abe, Saitama (JP)

(73) Assignee: Fujinon Corporation, Saitama (JP)

( * ) Notice: Subject to any disclaimer, the term of this patent is extended or adjusted under 35 U.S.C. 154(b) by 506 days.

(21) Appl. No.: 11/038,262

(22) Filed: Jan. 21, 2005

(65) Prior Publication Data

US 2005/0165274 A1 Jul. 28, 2005

(30) Foreign Application Priority Data

Jan. 27, 2004 (JP) ............................ 2004-018898

(51) Int. Cl.
*A61B 1/04* (2006.01)
*H04N 7/18* (2006.01)

(52) U.S. Cl. .................. 600/118; 600/109; 348/74; 348/75

(58) Field of Classification Search ............... 600/109, 600/118; 348/65, 72, 74; 200/43.01, 43.02
See application file for complete search history.

(56) References Cited

U.S. PATENT DOCUMENTS

| | | | | |
|---|---|---|---|---|
| 5,951,462 A | * | 9/1999 | Yamanaka | 600/118 |
| 6,184,922 B1 | * | 2/2001 | Saito et al. | 348/65 |
| 6,432,041 B1 | * | 8/2002 | Taniguchi et al. | 600/118 |
| 6,945,930 B2 | * | 9/2005 | Yokota | 600/118 |
| 2002/0175992 A1 | * | 11/2002 | Eino | 348/65 |

FOREIGN PATENT DOCUMENTS

| JP | 4-253830 | 9/1992 |
|---|---|---|
| JP | 2003-033322 | 2/2003 |

* cited by examiner

*Primary Examiner*—John P. Leubecker
(74) *Attorney, Agent, or Firm*—Snider & Associates; Ronald R. Snider

(57) ABSTRACT

A DVI circuit for generating a digital video signal in accordance with a display standard of a personal computer, etc. is provided for a processor device to which an electronic endoscope is connected. On the output side of the DVI circuit, a high vision system converter which is an adapter unit is connected as arbitrarily attached and removed using a connector. In the processor device, when the fixed state of a fixing screw is detected by a detection switch $SW_1$, and it is determined that the power supply line connected using a connector to the high vision system converter is in the energized state, a live line processing circuit activates a signal line of the connector. Thus, the adapter unit can be easily attached and removed without turning off the processor device.

3 Claims, 4 Drawing Sheets

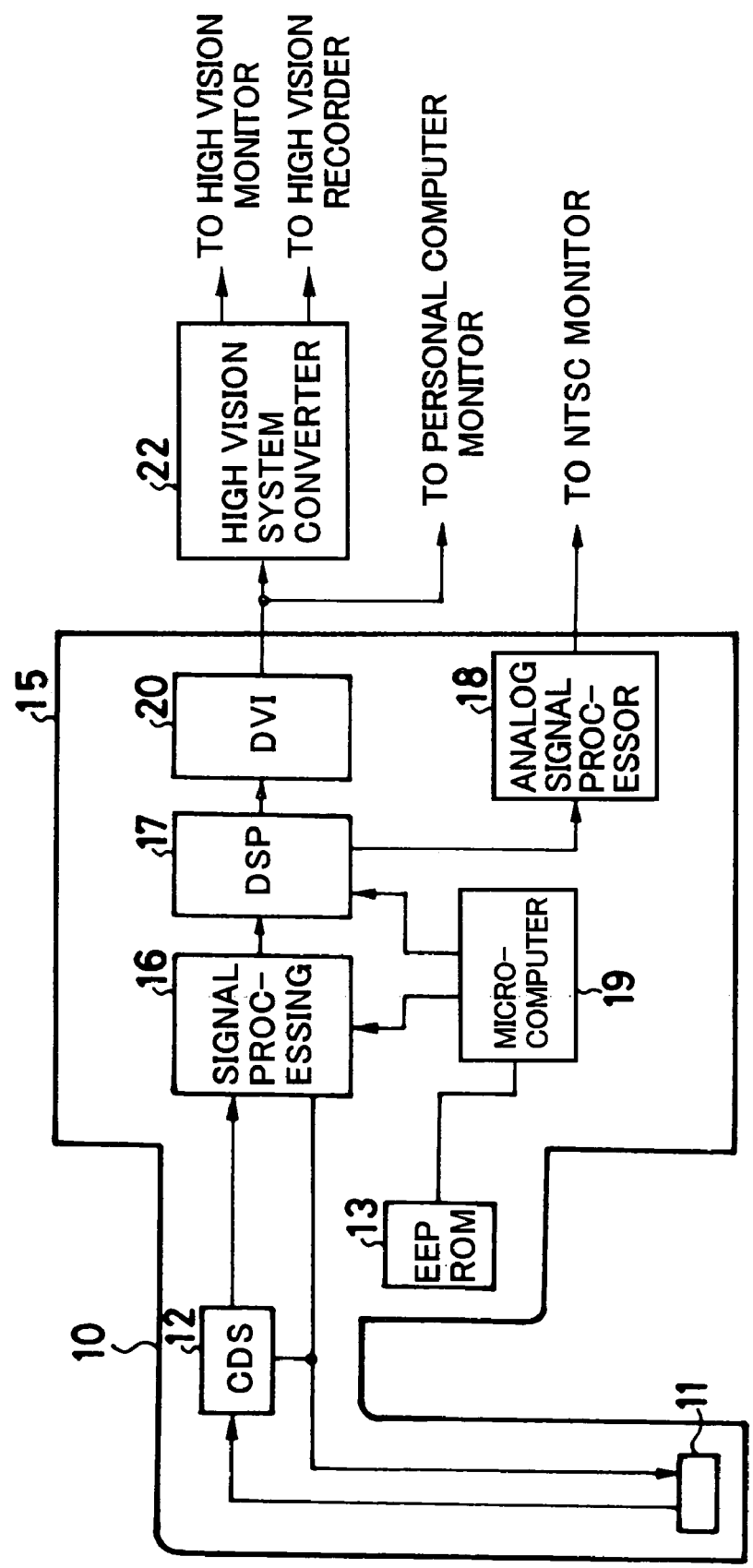

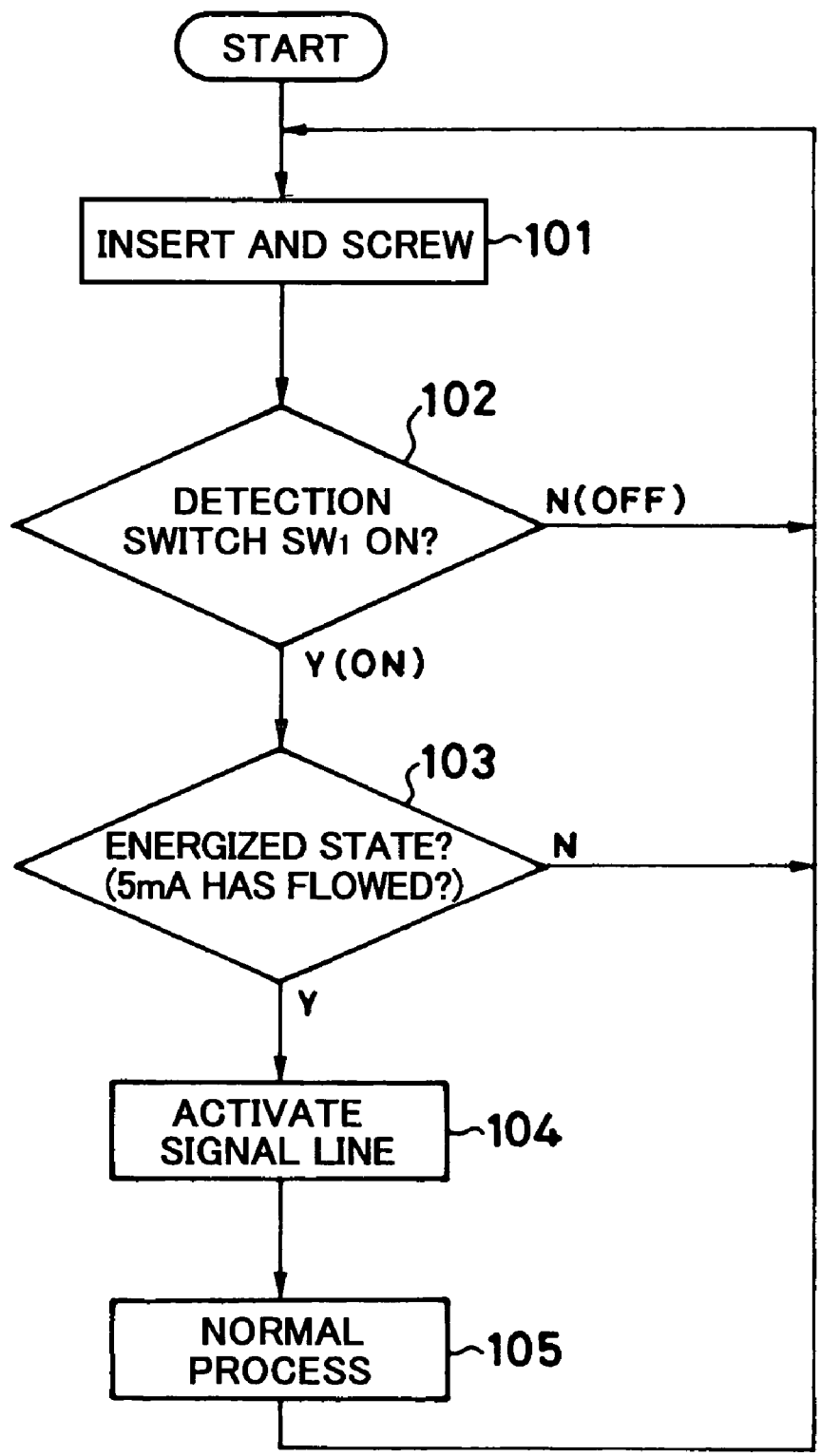

ELECTRONIC ENDOSCOPE APPARATUS FOR CONNECTION TO ADAPTER UNIT

BACKGROUND OF THE INVENTION

The application claims the priority of Japanese Patent Applications No. 2004-18898 filed on Jan. 27, 2004 which is incorporated herein by reference.

FIELD OF THE INVENTION

The present invention relates to an electronic endoscope apparatus, and more specifically to the configuration of an electronic endoscope apparatus with an adapter unit such as a high vision system converter, etc. attached to and removable from a processor device for inputting a capture signal obtained by a solid-state image pickup element and performing various types of image processing.

DESCRIPTION OF THE RELATED ART

An electronic endoscope apparatus is loaded with a CCD (charge coupled device), etc. which is a solid-state image pickup element at the tip portion of an electronic endoscope (electronic scope). The CCD captures an image of an observation object using the illumination of the light from the light supply device. A capture signal obtained by the CCD of the electronic endoscope is output to the processor device, and the processor device performs image processing. As a result, an image of an observation object can be displayed on the monitor, and a still image, etc. can be recorded on a recorder.

Normally, the above-mentioned image of an observation object is displayed on the NTSC monitor (aspect ratio of 3:4), which is a standard television system. For example, as described in Japanese Patent Laid-open Publication No. 4-253830, an image of an observation object is displayed on the monitor (aspect ratio of 9:16) in a high-quality high vision television (HDTV) system having about the double number of scanning lines. In the electronic endoscope apparatus, since a normal NTSC signal (analog signal) is formed from an output signal of a CCD, the NTSC signal is converted to a high vision television signal.

On the other hand, a still image (digital signal) of an observation object obtained by the electronic endoscope apparatus is recorded on the record medium in the filing device such as a personal computer, etc., and displayed and observed later on the personal computer monitor, and simultaneously the CCD uses an image of a large number of pixels indicating high resolution.

SUMMARY OF THE INVENTION

As described above, the CCD, which is a solid-state image pickup element, has recently been realized as device for an image of a high resolution having a large number of pixels. Therefore, in displaying an image in the high vision television system, there is the advantage of observing a higher-quality image of an observation object as compared with the conventional technology. However, if an NTSC signal is converted to a high vision television signal as described above, there is the restriction by the resolution of the NTSC video signal, and the resolution of the CCD indicating high-quality image cannot be fully utilized.

Furthermore, the CCD for different numbers of pixels is loaded for the electronic endoscope, and if the difference in the number of pixels of the CCD and a change for a large number of pixels are supported by the arrangement or update (exchange) of a conversion circuit for a high vision television signal in a processor device, then the entire system is costly and generates an expensive apparatus. Additionally, equipment for use in a medical field is requested to meet strict standards on the EMC (electromagnetic compatibility) and electric safety, and it is not practical to satisfy the medical standards in a dedicated large device such as a personal computer, etc. for conversion to a high vision television signal.

Therefore, the Applicant proposes a high vision system converter of adapter type by using video output digitized for supply to a personal computer, etc., connecting an electronic endoscope loaded with solid-state image pickup elements having different numbers of pixels, and obtaining an image of a high vision television system without degrading the resolution.

In attaching and removing an adapter unit such as a high vision system converter, it is convenient if electrical connection can be made safely without turning off the power supply to the processor device because the adapter unit can be quickly attached and removed regardless of the use state of the electronic endoscope. With the above-mentioned processor device, a connector is arranged for attachment/removal of an adapter unit. When the adapter is connected to the connector, a connector pin functions as an antenna, thereby causing the problem of undesired electromagnetic wave noise.

The present invention has been developed to solve the above-mentioned problem, and aims at providing an electronic endoscope apparatus capable of easily attaching to and removing from it an adapter unit such as a high vision system converter, etc. without turning off the processor device, and prevent the radiation of undesired electromagnetic wave noise from connector unit.

To attain the above-mentioned advantage, the present invention includes: an electronic endoscope loaded with a solid-state image pickup element for capturing an observation object; a processor device for performing various types of video processing on a video signal input from the electronic endoscope; an adapter unit configured to be connected to a connector unit of the processor device and fixed by a fixture, for performing predetermined signal processing; a fixed state detection mean for detecting whether or not the adapter unit is fixed to the processor device with the fixture; a live line processing circuit for setting a live line/non-live line of a signal line in the connector unit of the processor device; and a control circuit for activating a signal line of the connector unit of the processor device by the live line processing circuit when a fixed state of the adapter unit is determined from output of the fixed state detection means, and it is determined that a power supply line of the connector unit of the adapter unit is in a energized state.

In this case, a fixing screw is used as the fixture, and the fixed state detection means can be a detection switch for controlling the on and off state by moving a movable unit by a press of the fixing screw.

With the above-mentioned configuration, for example, an adapter unit of a high vision system converter can be connected by a connector into a dedicated slot provided in a processor device, and when the adapter unit arranged at the slot and attached to the processor device with a fixing screw, the fixing screw sets the detection switch in the ON position. On the other hand, when the control unit determines the attachment by the fixing screw using the detection switch and the energized state of the power supply line with the connector, the signal line is activated. With this configuration, since the power supply line and the signal line are not electrically connected simultaneously, the processor device and the adapter unit are not damaged, and the electrical safety is guaranteed. When the adapter unit is not attached, the control unit does not activate a signal line (including a connector terminal pin) although the cover of the slot is attached with a fixing screw. Therefore, the radiation of the electromagnetic wave noise from the connector unit can be prevented.

According to the electronic endoscope apparatus of the present invention, the electrical safety can be guaranteed with the power supply line connected to the processor device, and the adapter unit such as the high vision system converter, etc. can be easily attached and removed. When the adapter unit is not connected, the signal line of the connector unit enters the non-live line state, and the connector terminal (pin) functions as an antenna and the radiation of undesired electromagnetic wave noise can be prevented.

BRIEF DESCRIPTION OF THE DRAWINGS

FIG. 4 is a block diagram of the circuit showing the entire configuration of the electronic endoscope apparatus according to an embodiment of the present invention; and FIG. 5 is a flowchart of the operation according to an embodiment of the present invention.

DETAILED DESCRIPTION OF THE PREFERRED EMBODIMENTS

Figure 1:
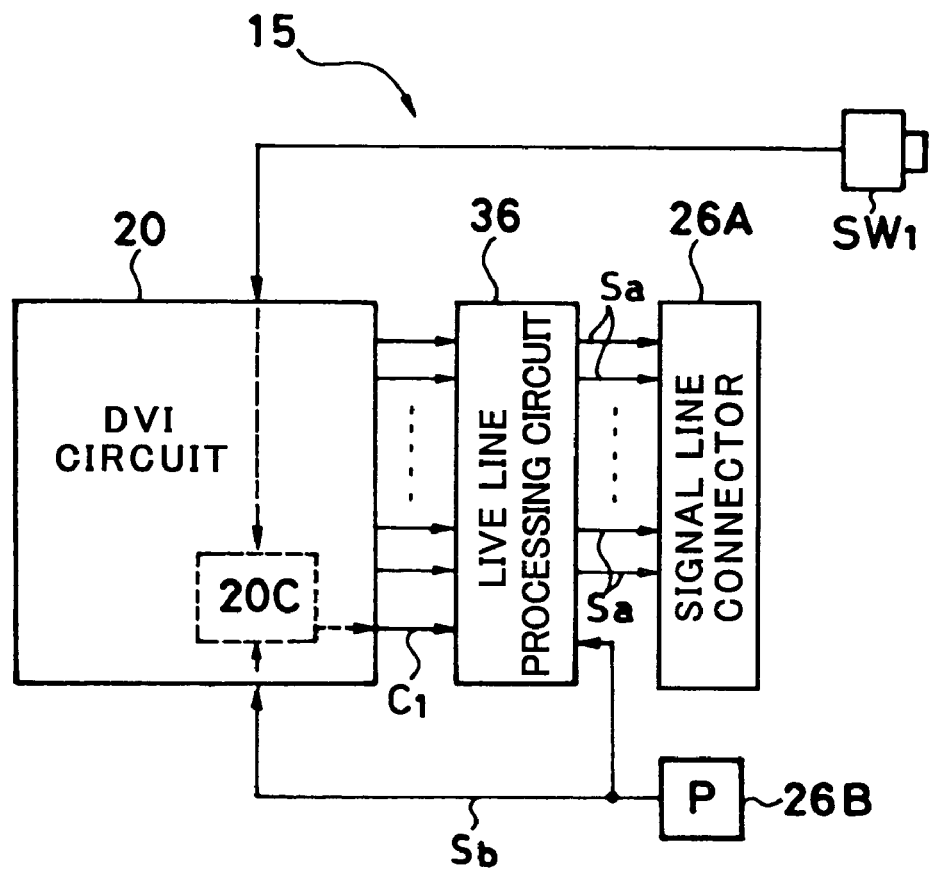
FIG. 1 is a block diagram of the circuit configuration relating to the live line processing of the electronic endoscope apparatus (processor device) according to an embodiment of the present invention.

FIGS. 1 to 4 show the configurations of the electronic endoscope apparatus according to the first embodiment of the present invention. The entire configuration of the apparatus is first described below. In FIG. 4, an electronic endoscope (electronic scope) 10 is provided with CCDs 11 which are solid-state image pickup elements at the tip portion. The CCDs 11 can be various types for 400 thousand pixels, 800 thousand pixels, 1.31 million pixels, etc. A duplex correlation sampling (CDS) circuit 12 for sampling a capture signal output from the CCD 11, memory (EEPROM) 13 for storing the identification information about the electronic endoscope 10, video processing information, etc. are also provided. The light of the light source device not shown in the attached drawings is supplied to the electronic endoscope 10 through a light guide, and an image of an observation object is captured by the CCD 11 by the illumination from the tip portion. Various electronic endoscopes 10 loaded with the CCD 11 having different number of pixels (or different transfer systems of the CCDs corresponding to the number of pixels) are connected to and arbitrarily removed from a processor device 15.

The processor device 15 comprises: a signal processing circuit 16 for performing various types of signal processing for generating a video signal; a DSP (digital signal processor) 17 for performing further video processing on a digitized video signal; an analog signal processor 18 for converting a video signal digitized by the DSP 17 to an analog signal (Y/C signal, etc.); and a microcomputer 19 for performing various types of control. At the stage subsequent to the DSP 17, a DVI (digital visual interface) circuit 20 is provided. The DVI circuit 20 generates a video signal in accordance with the display standard, for example, 640×480 (VGA: video graphics array), 1024×768 (XGA: extended graphics array), 1280×960, 1280×1024 (SXGA: super XGA), etc. for output to a personal computer monitor, etc., then parallel-serial converts the signal, and outputs the serial signal as a differential signal to a personal computer monitor, a filing device, etc. The DVI is a high-speed display interface set by DDWG (digital display working group), and adopts TMDS (transition minimized differential signaling) as a data format.

A high vision system converter 22 is provided as forming the adapter unit by connection to the output connector unit of the DVI circuit 20, and the output of the high vision system converter 22 is connected to the HDTV monitor and the HDTV recorder. That is, the high vision system converter 22 comprises frame memory, etc. for storing an input video signal, detects the number of pixels from the horizontal synchronous signal (H) and the vertical synchronous signal (V) of the video signal, and reads the video signal from the frame memory by control of a memory read depending on the number of pixels, thereby generating a high vision television signal (Y, Pr, Pb signals).

Figure 3:
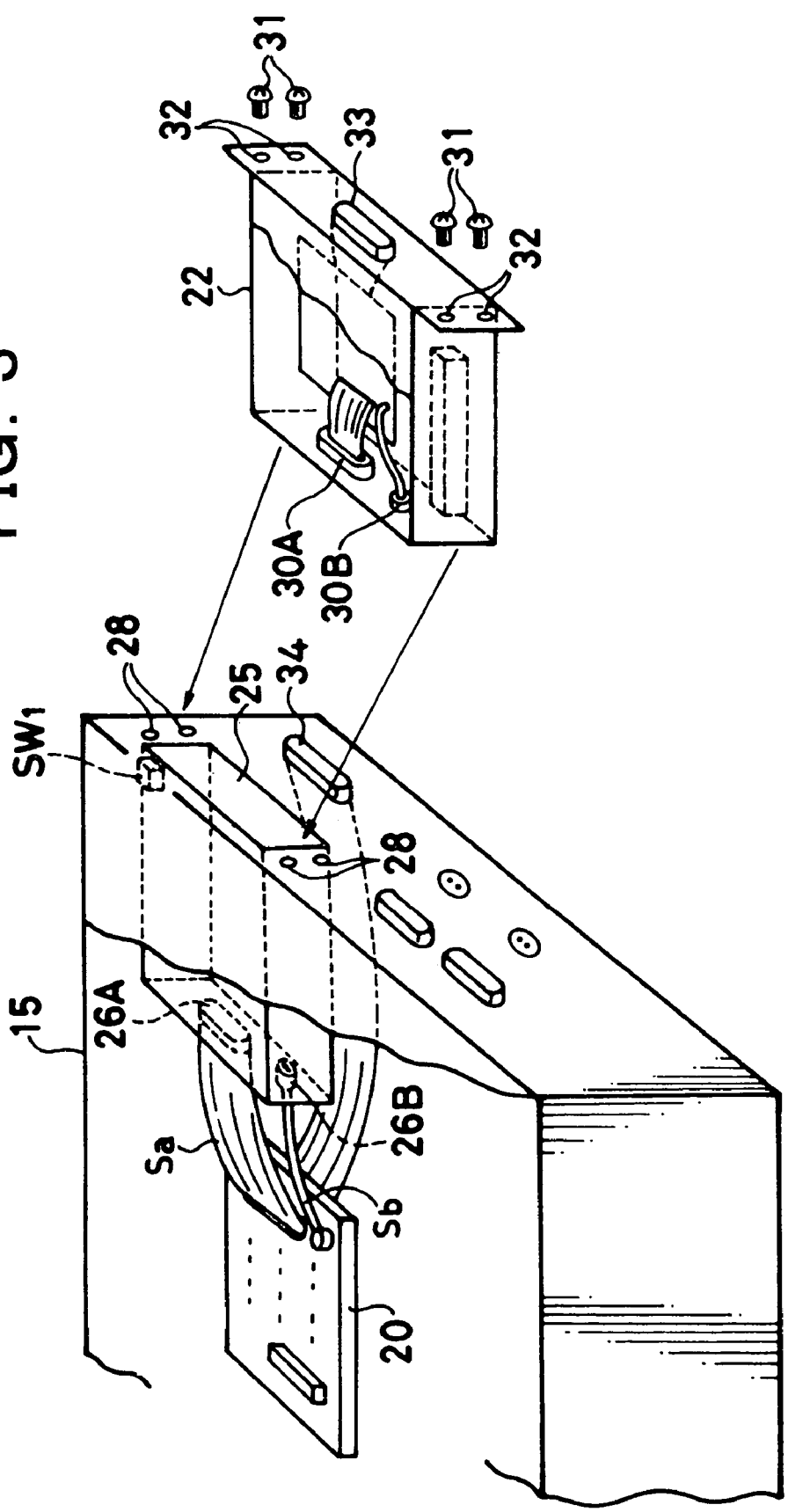
FIG. 3 is a perspective view showing the configuration of the attachment connection units of the processor device and the high vision system converter (adapter unit)

FIG. 3 shows the configurations of the attachment connection units of the processor device 15 and the high vision system converter (adapter unit) 22. As shown in FIG. 3, a high vision system converter slot 25 is provided on the back of the processor device 15. On the front of the slot 25, a signal line connector (for example, on the male side) 26A and a power supply line connector (male side) 26B for the connection to the high vision system converter 22 are provided, and the DVI circuit (board) 20 is connected to the connectors 26A and 26B through a signal line Sa and a power supply line Sb. On the reverse side of one of screw holes 28, a detection switch $SW_1$ is provided as fixed state detection means.

On the other hand, the high vision system converter 22 is provided with a signal line connector (for example, the female side) 30A and a power supply line connector (female side) 30B for connection to the processor device 15, and an insertion hole 32 of a fixing screw 31 is provided. On the back of the high vision system converter 22, a connector 33 for output to a high vision monitor, etc. is provided. A connector 34 is provided on the back of the processor device 15 for output to a personal computer monitor, etc.

FIG. 1 shows the configuration relating to the live line processing in the processor device 15, and a live line processing circuit 36 is connected between a control circuit 20C arranged in the DVI circuit 20 shown in FIG. 3 and the signal line connector 26A. The live line processing circuit 36 connects, for example, a three state buffer, etc. to each signal line Sa, and sets it as either a live line or a non-live line. Additionally, it connects mechanical switches, etc. to each signal line Sa, thereby switching between a live line and a non-live line.

Figure 2A:
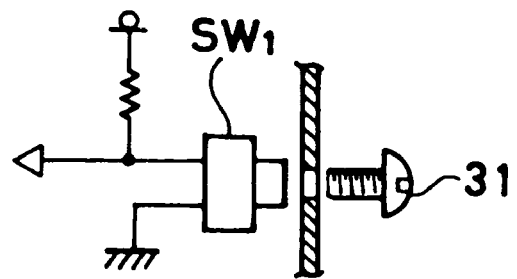
FIG. 2A shows the relationship between the detection switch and the fixing screw when the fixing screw is removed.
Figure 2B:
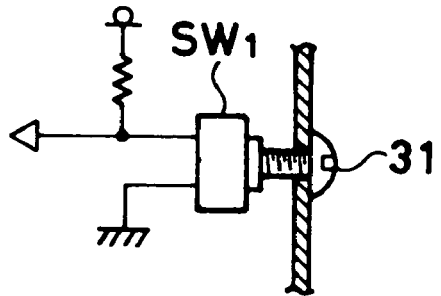
FIG. 2B shows the relationship between the detection switch and the fixing screw when the fixing screw is attached.

The embodiment is configured as described above, and its operation is explained by referring to FIGS. 5 and 2. As shown in FIG. 3, the high vision system converter 22 as an adapter unit is attached by inserting it into the high vision system converter slot 25 of the processor device 15, and coupling the fixing screw 31 to the screw hole 28 through the insertion hole 32. In FIG. 5, when the high vision system converter 22 is inserted and screwed (step 101), it is determined in step 102 whether or not the detection switch $SW_1$ is turned on. When the fixing screw 31 turns on the detection switch $SW_1$ (Y (YES)) as shown in FIG. 2B, it is determined in step 103 that the power supply line is in the energized state by coupling power supply line connectors 26B and 30B. It is determined by detecting the status of the flow of, for example, 5 mA in the power supply line Sb. If YES, the signal line is activated in step 104. Afterwards, a normal process is performed (step S105).

That is, as shown in FIG. 1, when the control circuit 20C of the DVI circuit 20 receives an ON signal from the detection switch $SW_1$ and determines that current flows through the power supply line Sb connected to the power supply line connector 26B, the control circuit 20C operates the live line processing circuit 36 by the control signal provided through a control line $C_1$, and sets the signal line Sa in the live line state. On the other hand, the high vision system converter 22 is removed by first removing the fixing screw 31 as shown in FIG. 2A. Therefore, the detection switch $SW_1$ enters the OFF status. As a result, before the power supply line connectors 26B and 30B are removed, the signal line Sa is activated by the live line processing circuit 36. Thus, the supply of electric power by the power supply line Sb and the transmission of a signal by the signal line Sa electrically enter an energized state and a non-energized state with different timing. Therefore, the high vision system converter 22 can be easily attached or removed without ill effects on the internal circuit of the DVI circuit 20 and the high vision system converter 22.

When the high vision system converter 22 is not attached, the dedicated high vision system converter slot 25 is vacant, and it is desired that a planar cover prepared at the entrance of the high vision system converter slot 25 is fixed with the fixing screw 31. However, in this case, only the attachment with the fixing screw 31 does not activates the signal line Sa. Therefore, advantageously, the pin, etc. of the signal line connector 26A does not function as an antenna or radiate undesired electromagnetic wave noise.

With the high vision system converter 22, a video signal of a display standard such as, for example, 640×480 (VGA), 1024×768 (XGA), 1280×960, 1280×1024 (SXGA), etc. generated using the personal computer monitor as an output object is converted to a high vision television signal, and the video signal can be output to a high vision monitor and a high vision recorder. Thus, an observation object obtained by an endoscope can be observed as a high vision image.

Furthermore, according to the above embodiment of the present invention, the high vision system converter 22 is connected to the processor device 15, but an adapter unit having other functions can be removably attached to the processor device 15.

What is claimed is:

1. An electronic endoscope apparatus, comprising:
   an electronic endoscope loaded with a solid-state image pickup element for capturing an observation object;
   a processor device for performing various types of video processing on a video signal input from the electronic endoscope;
   an adapter unit configured to be connected to a connector unit of the processor device and fixed by a fixture, for performing predetermined signal processing;
   a fixed state detection means for detecting whether or not the adapter unit is fixed to the processor device with the fixture;
   a live line processing circuit for setting a live line/non-live line of a signal line in the connector unit of the processor device; and
   a control circuit for activating a signal line of the connector unit of the processor device by the live line processing circuit when a fixed state of the adapter unit is determined from output of the fixed state detection means, and it is determined that a power supply line of the connector unit is in a energized state.

2. The electronic endoscope apparatus according to claim 1, further comprising
   a fixing screw as the fixture, and a detection switch for controlling on and off states by moving a movable unit by a press of the fixing screw as the fixed state detection means.

3. The electronic endoscope apparatus according to claim 1, further comprising a high vision system converter for converting an image obtained by various electronic endoscopes loaded with solid-state image pickup elements having different number of pixels as adapter units to a high vision television system, and the high vision system converter is connected with a connector to a differential signal output unit of the processor device for generating a video signal in accordance with a personal computer monitor.

* * * * *